United States Patent

Fliri et al.

[11] Patent Number: 5,883,094
[45] Date of Patent: Mar. 16, 1999

[54] BENZIMIDAZOLONE DERIVATIVES WITH CENTRAL DOPAMINERGIC ACTIVITY

[75] Inventors: Anton F-J. Fliri, Norwich; Brian T. O'Neill, Old Saybrook; William S. Faraci, East Lyme; Mark A. Sanner, Old Saybrook; Stevin H. Zorn, North Stonington, all of Conn.

[73] Assignee: Pfizer Inc., New York, N.Y.

[21] Appl. No.: 750,479

[22] PCT Filed: Apr. 24, 1995

[86] PCT No.: PCT/IB95/00285

§ 371 Date: Mar. 11, 1997

§ 102(e) Date: Mar. 11, 1997

[87] PCT Pub. No.: WO95/34555

PCT Pub. Date: Dec. 21, 1995

Related U.S. Application Data

[63] Continuation-in-part of Ser. No. 259,707, Jun. 14, 1995, abandoned.

[51] Int. Cl.⁶ .................. C07D 403/14; C07D 401/14; A61K 31/53; A61K 31/50
[52] U.S. Cl. .......... 514/242; 514/253; 514/318; 544/182; 544/357; 544/238; 544/360; 546/194
[58] Field of Search .................... 544/295, 182, 544/357, 238, 360; 546/194; 514/242, 253, 318

[56] References Cited

U.S. PATENT DOCUMENTS

| | | | |
|---|---|---|---|
| 3,634,441 | 1/1972 | Wellstead, Jr. et al. | 260/299 B |
| 3,794,651 | 2/1974 | Heisley et al. | 260/268 BC |
| 4,200,641 | 4/1980 | Vandenberk et al. | 424/627 |
| 4,250,176 | 2/1981 | Vanderberk et al. | 424/250 |
| 4,254,127 | 3/1981 | Vandenberk et al. | 424/263 |
| 4,377,578 | 3/1983 | Vanderberk et al. | 424/250 |
| 5,576,318 | 11/1996 | Bietti et al. | 514/253 |

FOREIGN PATENT DOCUMENTS

| | | |
|---|---|---|
| 0571174 | 10/1992 | European Pat. Off. |
| 0526434 | 2/1993 | European Pat. Off. |
| 2017265 | 10/1970 | Germany |
| 2714437 | 10/1979 | Germany |

OTHER PUBLICATIONS

Hubert H.M. Van Tol, et al., in *Nature*, vol. 350, No. 3619, pp. 610–614 (1991).
C.J. Schmidle et al., in *Journal of the American Chemical Society*, vol 78, p. 1702 (1956).
K–Y Tserng et al., in *Journal of Organic Chemistry*, vol. 38, p. 3498 (1973).
D.A. Evans et al., in *Tetrahedron Letters*, vol. 23, p. 285 (1982).
R.K. Sunahara et al., in *Nature*, vol. 347, pp. 80–83 (1990).
Pamela L. Moriearty, CNS Drugs (1995), Chemical Abstracts vol. 124, Abstract No. 105259, 1995.

*Primary Examiner*—Matthew V. Grumbling
*Attorney, Agent, or Firm*—Peter C. Richardson; Paul H. Ginsburg; Karen Debenedictis

[57] ABSTRACT

This invention relates to novel, pharmaceutically active benzimidazolone derivatives of the formula

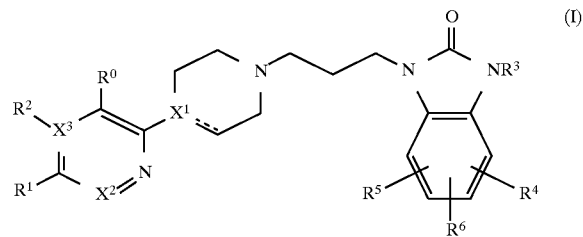

wherein the dashed line, $R^0$ through $R^6$ and $X^1$ through $X^3$ are defined as in the specification. These compounds exhibit central dopaminergic activity and are u in the treatment of CNS disorders.

15 Claims, No Drawings

BENZIMIDAZOLONE DERIVATIVES WITH CENTRAL DOPAMINERGIC ACTIVITY

CROSS REFERENCE TO RELATED APPLICATIONS

This application is a 371 of PCT/IB95/00285, filed Apr. 24, 1995, which, in turn, is a continuation-in-part in of U.S. patent application Ser. No. 08/259,707, filed Jun. 14, 1995 and now abandoned.

BACKGROUND OF THE INVENTION

The present invention relates to novel pharmacologically active benzimidazolone derivatives and their acid addition salts. The compounds of this invention exhibit central dopaminergic activity and are useful in the treatment of central nervous system (CNS) disorders. They act preferentially on the D4 dopamine receptor.

It is generally accepted knowledge that dopamine receptors are important for many functions in the animal body. For example, altered functions of these receptors participate in the genesis of psychosis, addiction, sleep, feeding, learning, memory, sexual behavior, regulation of immunological responses and blood pressure. Since dopamine receptors control a great number of pharmacological events and, on the other hand, not all of these events are presently known, there is a possibility that compounds that act preferentially on the D4 dopamine receptor may exert a wide range of therapeutic effects in humans.

European Patent Application EP 526434, which was published on Feb. 3, 1993, refers to a class of substituted benzimidazolones that contain 1-(aryl and heteroaryl)-4-propyl piperidine substituents. These compounds were found to exhibit an affinity for the $5HT_{1A}$ and $5HT_2$ serotonin receptors. German Patent Application DE 2714437, which was published on Oct. 20, 1977, refers to a series of 1-[3-(4-benzhydryl)piperazin-1-yl]propyl-2,3-dihydro-1H-benzimidazol-2-ones and reports that such compounds exhibited antihistamine activity when tested in mice. German Patent Application DE 2017265, which was published on Oct. 15, 1970, refers to a class of substituted 1-[3-(4-phenyl)piperazin-1-yl]propyl-2-methyl-1H-benzimidazoles that were found to exhibit bronchodilating effects in mice. European Patent Application EP 511074A1, which was published on Oct. 28, 1992, refers to benzimidazolone derivatives that are $5HT_2$ serotonin receptor antagonists useful in the treatment of a variety of CNS disorders.

The present invention relates to several substituted 1-[3-(4-heteroaryl)piperazin-1-yl)propyl]2,3-dihydro-1H-benzimidazol-2-ones that posess central dopaminergic activity and which have been found to have a preference for the D4 dopamine receptor.

SUMMARY OF THE INVENTION

This invention relates to compounds of the formula I

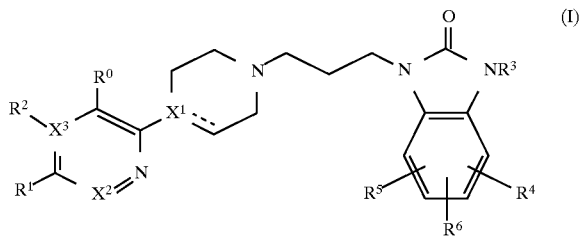

wherein $X^1$, $X^2$ and $X^3$ are independently selected from carbon and nitrogen;

$R^0$, $R^1$ and $R^2$ are independently selected from hydrogen, halo (e.g., chloro, fluoro, bromo or iodo), $(C_1-C_6)$alkyl optionally substituted with from one to three fluorine atoms and $(C_1-C_6)$alkoxy optionally substituted with from one to three fluorine atoms;

$R^3$ is hydrogen, $(C_1-C_6)$alkyl or benzyl, wherein the phenyl moiety of said benzyl group may optionally be substituted with from one or more substituents, preferably with from one to three substituents, independently selected from halo (i.e., chloro, fluoro, bromo or iodo), cyano, $(C_1-C_6)$alkyl optionally substituted with from one to three fluorine atoms, $(C_1-C_6)$alkoxy optionally substituted with from one to three fluorine atoms, $(C_1-C_6)$alkylsulfonyl, $(C_1-C_6)$alkylamino, amino, di-$(C_1-C_6)$alkylamino and $(C_1-C_6)$carboxamido;

$R^4$, $R^5$ and $R^6$ are independently selected from hydrogen, halo (e.g., chloro, fluoro, bromo or iodo), cyano, $(C_1-C_6)$alkyl optionally substituted with from one to three fluorine atoms, $(C_1-C_6)$alkoxy optionally substituted with from one to three fluorine atoms, $(C_1-C_6)$alkylsulfonyl, $(C_1-C_6)$acylamino, (phenyl)[$(C_1-C_6)$acyl]amino, amino, $(C_1-C_6)$alkylamino and di-$(C_1-C_6)$alkylamino; and the dashed line represents an optional double bond;

with the proviso that when $X^3$ is nitrogen, $R^2$ is absent.

The compounds of formula I that are basic in nature are capable of forming a wide variety of salts with various inorganic and organic acids. The acids that may be used to prepare pharmaceutically acceptable acid addition salts of those compounds of formula I that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

This invention also relates to the pharmaceutically acceptable acid addition salts of compounds of the formula I.

The term "one or more substituents", as used herein, includes from one to the maximum number of substituents possible based on the number of available bonding sites.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O—alkyl, wherein "alkyl" is defined as above.

Preferred compounds of this invention include compounds of the formula I, wherein $R^1$ is bromine and $X^2$ is nitrogen.

Other preferred compounds of this invention include compounds of the formula I, wherein $R^1$ is chlorine and $X^2$ is nitrogen.

Examples of specific preferred compounds of this invention include the following:

1-[3-(4-pyridin-2-yl-piperazin-1-yl)-propyl]-1,3-dihydro-benzoimidazol-2-one;

1-{3-[4-(5-trifluoromethyl-pyridin-2-yl)-piperazin-1-yl]-propyl}-1,3-dihydro-benzoimidazol-2-one;

1-{3-[4-(5-chloro-pyridin-2-yl)-piperazin-1-yl]-propyl}-1,3-dihydro-benzoimidazol-2-one;

1-{3-[4-(5-bromo-pyridin-2-yl)-piperazin-1-yl]-propyl}-1,3-dihydro-benzoimidazol-2-one;

1-[3-(2,3,5,6-tetrahydro-[1,2']bipyrazinyl4-yl)-propyl]-1,3-dihydro-benzoimidazol-2-one; and 1-{3-[4-(6-chloro-pyridazin-3-yl)-piperazin-1-yl]-propyl}-1,3-dihydro-benzoimidazol-2-one.

Other embodiments of this invention include:

compounds of the formula I wherein $X^2$ is carbon, $X^3$ is nitrogen and $R^1$ is hydrogen or substituted or unsubstituted alkoxy;

compounds of the formula I wherein $X^2$ and $X^3$ are both carbon and $R^1$ is hydrogen or substituted or unsubstituted alkoxy;

compounds of the formula I wherein $X^1$ is carbon;

compounds of the formula I wherein $X^2$ and $X^3$ are both carbon and each of $R^0$, $R^1$ and $R^2$ is other than a fluoroalkyl group; and compounds of the formula I wherein $X^1$ is nitrogen.

Other compounds of this invention include the following:

1-[2-cyano-3-(2,3,5,6-tetrahydro-[1,2']bipyrazinyl-4-yl)-propyl]-1,3-dihydro-benzoimidazol-2-one;

1-[5-methyl,3-(2,3,5,6-tetrahydro-[1,2']bipyrazinyl-4-yl)-propyl]-1,3-dihydro-benzoimidazol-2-one;

1-[6-cyano,3-(2,3,5,6-tetrahydro-[1,2']bipyrazinyl-4-yl)-propyl]-1,3-dihydro-benzoimidazol-2-one;

1-{3-[4-(5-fluoro-pyridin-2-yl]-propyl]-3-methyl-1,3-methyl-1,3-dihydro-benzoimidazol-2-one;

1{3-[4-(3-cyano-pyridin-2-yl)-piperazin-1-yl]-propyl]-1,3-dihydro-benzoimidazol-2-one;

1-(3-[4-(4-cyano-pyridin-2-yl)-piperazin-1-yl]-propyl]-1,3-dihydro-benzoimidazol-2-one;

1-{3-[4-(6-trifluoromethyl-pyridin-2-yl)-piperazin-1-yl]-propyl}-1,3-dihydro-benzoimidazol-2-one;

1-{3-[4-(5-fluoro-pyridin-2-yl)-piperazin-1-yl]-propyl}-5-fluoro-1,3-dihydro-benzoimidazol-2-one; and 1-{3-[4-(5,fluoro-pyridin-2-yl)-piperazin-1-yl]-propyl}-5,6-difluoro-1,3-dihydro-benzoimidazol-2-one.

The compounds of formula I above may contain chiral centers and therefore may exist in different enantiomeric forms. This invention relates to all optical isomers and all other stereoisomers of compounds of the formula I and mixtures thereof.

Formula I above includes compounds identical to those depicted but for the fact that one or more hydrogens or carbon atoms are replaced by isotopes thereof. Such compounds are useful as research and diagnostic tools in metabolism pharmacokinetics studies and in binding assays.

This invention also relates to a pharmaceutical composition for treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising an amount of a compound of the formula I, or pharmaceutically acceptable salt thereof, that is effective in treating or preventing such condition, and a pharmaceutical acceptable carrier.

The present invention also relates to a method of treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising administering to said mammal an amount of a compound of the formula I, or pharmaceutically acceptable salt thereof, that is effective in treating or preventing such condition.

The present invention also relates to a pharmaceutical composition for treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising a dopaminergic effective amount of a compound of the formula I, or a pharmaceutically acceptable salt thereof, and a pharmaceutically acceptable carrier.

The present invention also relates to a method of treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, cardiovascular and ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising an administering to said mammal a dopaminergic effective amount of a compound of the formula I, or pharmaceutically acceptable salt thereof.

This invention also relates to a pharmaceutical composition for treating or preventing a disease or condition, the treatment or prevention of which can be effected or facilitated by altering dopamine mediated neurotransmission in a mammal, including a human, comprising a dopaminergic effective amount of a compound of the formula I, or a pharmaceutically acceptable salt thereof, and a pharmaceutically acceptable carrier.

This invention also relates to a method of treating or preventing a disease or condition, the treatment or prevention of which can be effected or facilitated by altering dopamine mediated neurotransmission in a mammal, including a human, comprising administering to said mammal a dopaminergic effective amount of a compound of the formula I, or a pharmaceutically acceptable salt thereof.

The present invention also relates to a pharmaceutical composition for treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising a D4 receptor binding effective amount of a compound of the formula I, or a pharmaceutically acceptable salt thereof, and a pharmaceutically acceptable carrier.

The present invention also relates to a method of treating or preventing a condition selected from sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, schizoaffective disorder, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation in a mammal, including a human, comprising an administering to said mammal a D4 receptor binding effective amount of a compound of the formula I, or pharmaceutically acceptable salt thereof.

This invention also relates to a pharmaceutical composition for treating or preventing a disease or condition, the treatment or prevention of which can be effected or facilitated by altering dopamine mediated neurotransmission in a mammal, including a human, comprising a D4 receptor binding effective amount of a compound of the formula I, or a pharmaceutically acceptable salt thereof, and a pharmaceutically acceptable carrier.

This invention also relates to a method of treating or preventing a disease or condition, the treatment or prevention of which can be effected or facilitated by altering dopamine mediated neurotransmission in a mammal, including a human, comprising administering to said mammal a D4 receptor binding effective amount of a compound of the formula I, or a pharmaceutically acceptable salt thereof.

The term "dopaminergic effective amount", as used herein, refers to an amount sufficient to inhibit the binding of dopamine to a dopamine receptor.

The term "altering dopamine mediated neurotransmission", as used herein, includes but is not limited to increasing or decreasing D4 dopamine receptor mediated neurotransmission.

DETAILED DESCRIPTION OF THE INVENTION

The preparation of compounds of the formula I are described below. In the reaction schemes and discussion that follows, $X^1$, $X^2$, $X^3$, $R^0$, $R^1$, $R^2$, $R^3$, $R^4_1$, $R^5$, and the dashed line are defined as above.

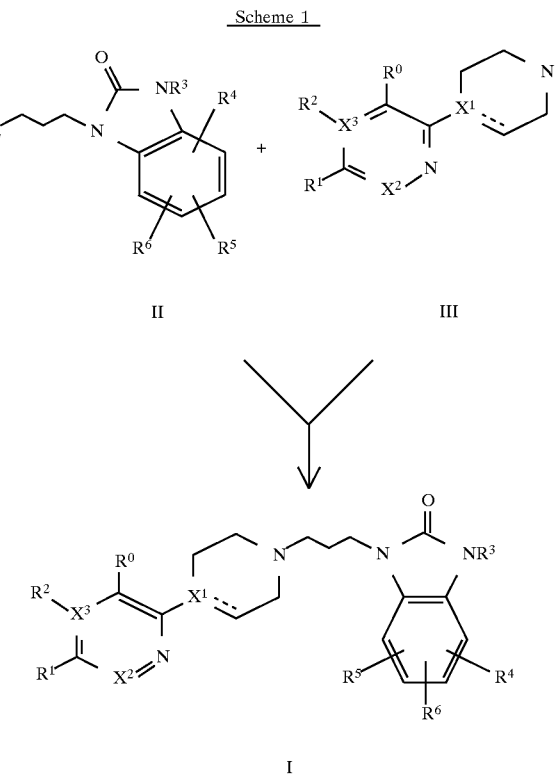

Scheme 2

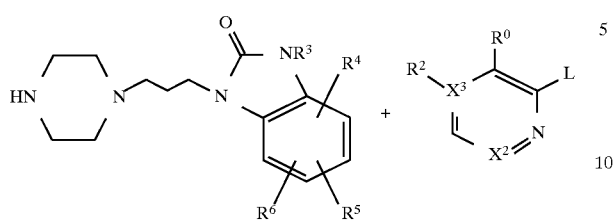

IV     V

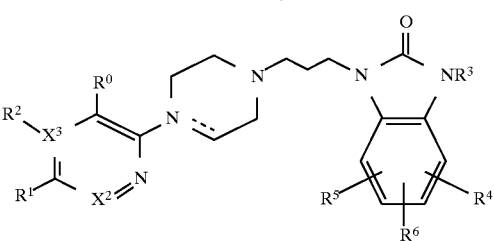

I

Scheme 3

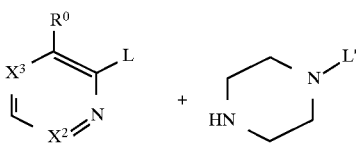

V     VI

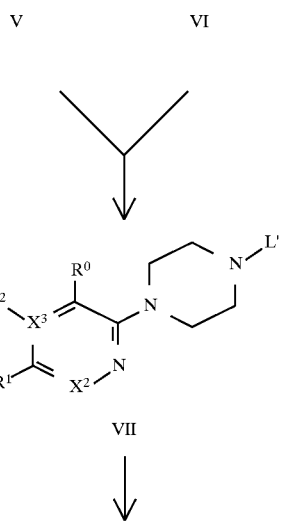

VII

Scheme 3 -continued

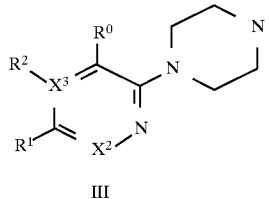

III

Scheme 4

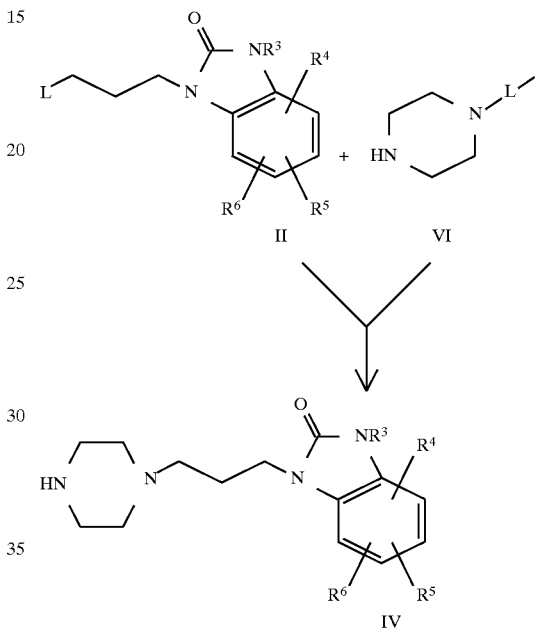

IV

Referring to scheme 1, a compound of the formula II, wherein L is an appropriate leaving group, is reacted with a compound of the formula III to form the corresponding desired compound of the formula I. Examples of suitable leaving groups "L" include chloro, bromo, iodo, —O—$(C_1$–$C_4)$alkylsulfonyl, and —O- phenylsulfonyl. This reaction is generally carried out in an inert polar solvent such as a lower alcohol, a cyclic or acyclic alkylketone (e.g., ethanol or acetone), an alkylester (e.g., ethylacetate), a cyclic or acyclic mono or dialkylamide (e.g., N-methylpyrrolidin-2-one or dimethylformamide (DMF)), a cyclic or acyclic alkyl ether (e.g., tetrahydrofuran (THF) or diisopropyl ether), or a mixture of two or more of the foregoing solvents, at a temperature from about 0° C. to about 150° C. It is preferably carried out in ethanol at a temperature from about 0° C. to about the reflux temperature.

Alternatively, compounds of the formula I wherein $X^1$ is nitrogen can be prepared by the method illustrated in scheme 2. Referring to scheme 2, compounds of the formula I may be formed by reacting a compound of the formula IV with the appropriate compound of the formula V, wherein L is defined above. Suitable solvents and temperatures for this reaction are similar to these described above for the reaction of compounds of the formulae II and Ill. Preferably, this reaction is conducted in DMF at about the reflux temperature.

Scheme 3 and 4 illustrate the synthesis of compounds of the formulae III and IV, respectively, which are used as reactants in the processes of schemes 1 and 2.

As depicted in scheme 3, a compound of the formula V is reacted with a compound of the formula VI, wherein L' is a suitable nitrogen protecting group, to form the corresponding compound of the formula VII, from which the protecting group is then removed to form the corresponding desired compound of the formula III wherein $X^1$ is nitrogen and the ring that contains $X^1$ is saturated. Examples of suitable nitrogen protecting groups include benzyl, benzyloxycarbonyl, t-butoxycarbonyl and trityl (triphenylmethyl). When L' is one of the foregoing named protecting groups, it may be conveniently removed by either hydrogenation, acidic conditions or both. Other conventionally used protecting groups may be introduced and removed using methods well known to those skilled in the art.

Compounds of the formula IIII wherein $X^1$ is other than nitrogen and the ring containing $X^1$ is saturated may be prepared as described in the literature. (See *Tetrahedron Letters*, 23, 285 (1982) and *J. Amer. Chem. Soc.*, 78, 1702 (1956). The foregoing literature references are incorporated herein by reference on their entireties.

Compounds of the formula III wherein the ring containing $X^1$ is unsaturated may be prepared from the corresponding compounds wherein the ring containing $X^1$ is unsaturated by using conventional hydrogenation methods that are well known to those skilled in the art (e.g., reacting such compounds with hydrogen gas under a pressure of about 2 atmospheres in the presence of a catalyst such as an oxide or complex containing platinum, palladium, rhodium or nickel).

The above reaction may be carried out using solvents or solvent mixture similar to those described above for formation of compounds of the formula I. It may also be carried out over the same temperature range (ie., from about 0° C. to about 150° C.). Preferably, this reaction is carried out in DMF at about the reflux temperature.

As indicated above, scheme 4 illustrates the preparation of compounds of formula IV wherein $X^1$ is nitrogen and the ring containing $X^1$ is saturated. Referring to scheme 4, the desired compound of formula IV can be prepared by reacting a compound of the formula VI, wherein L' is a leaving group, as defined above, with the appropriate compound of the formula II, wherein L is a leaving group, as defined above. Suitable solvents and temperatures for this reaction are the same as those described for the preparation of compounds of the formula I. The preferred solvent is ethanol and the preferred temperature is about the reflux temperature.

Compounds of the formula II, which are used as reactants in the process of scheme 1, are either commercially available or can be prepared as described in *J. Org. Chem.*, 38, 3498–502 (1973) and in European Patent Application EP 0526434, referred to above. Both these references are incorporated herein by reference in their entireties.

The preparation of other compounds of the formula I not specifically described in the foregoing experimental section can be accomplished using combinations of the reactions described above that will be apparent to those skilled in the art.

In each of the reactions discussed or illustrated in schemes 1 to 4 above, pressure is not critical unless otherwise indicated. Pressures from about 0.5 atmospheres to about 4 atmospheres are generally acceptable, and ambient pressure, i.e., about 1 atmosphere, is preferred as a matter of convenience.

The novel compounds of the formula I and the pharmaceutically acceptable salts thereof (hereinafter "the therapeutic compounds of this invention") are useful as dopaminergic agents, i.e., they possess the ability to decrease dopamine mediated neurotransmission in mammals, including humans. They are therefore able to function as therapeutic agents in the treatment of a variety of conditions in mammals, the treatment or prevention of which can be effected or facilitated by altering dopamine mediated neurotransmission. Such conditions include sleep disorders, sexual disorders (including sexual dysfunction), gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS such as meningitis, learning disorders, memory disorders, Parkinson's disease, depression, extrapyramidal side effects from neuroleptic agents, neuroleptic malignant syndrome, hypothalamic pituitary disorders, congestive heart failure, chemical dependencies such as drug and alcohol dependencies, vascular and cardiovascular disorders, ocular disorders, dystonia, tardive dyskinesia, Gilles De La Tourette's syndrome and other hyperkinesias, dementia, ischemia, Parkinson's disease, movement disorders such as akathesia, hypertension and diseases caused by a hyperactive immune system such as allergies and inflammation.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The therapeutic compounds of this invention can be administered orally, transdermally (e.g., through the use of a patch), parenterally, intranasally, sublingually, rectally or topically. Oral administration is preferred. In general, these compounds are most desirably administered in dosages ranging from about 0.5 mg to about 1000 mg per day, preferably from about 0.1 to about 250 mg per day, in single or divided doses, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The D4 dopaminergic activity of the compounds of the present invention may be determined by the following procedure.

The determination of D4 dopaminergic activity has been described by Van Tol et al., Nature, vol. 350, 610 (London, 1991). Clonal cell lines expressing the human dopamine D4 receptor are harvested and homogenized (teflon pestle) in a 50 mM Tris:HCl (pH 7.4 at 4° C.) buffer containing 5 mM EDTA, 1.5 mM calcium chloride ($CaCl_2$), 5 mM magnesium chloride ($MgCL_2$), 5 mM potassium chloride (KCl) and 120 mM sodium chloride (NaCl). The homogenates are centrifugated for 15 min. at 39,000 g, and the resulting pellets resuspended in a buffer at a concentration of 150–250 $\mu$g/ml. For saturation experiments, 0.25 ml aliquots of tissue homogenate are incubated in duplicate with increasing concentrations of [$^3$H] Spiperone (70.3 Ci/mmol; 10–3000 pM final concentration) for 30–120 minutes at 220° C. in a total volume of 1 ml. For competition binding experiments, assays are initiated by the addition of 0.25 ml of membrane and incubated in duplicate with the indicated concentrations of competing ligands ($10^{-14}$–$10^{-3}$M) and [$^3$H]Spiperone (100–300 pM) in either the absence or presence of 200 uM GPP(NH)$^p$ (5'/guanylylimidodiphosphate), where indicated, for 60–120 min at 220° C. Assays are terminated by rapid filtration through a Titertek cell harvester and the filters subsequently monitored for tritium as described by Sunahara, R. K. et al., Nature, 347, 80–83 (1990). For all experiments, specific [$^3$H]Spiperone binding is defined as that inhibited by 1–10 $\mu$M (+) Butaclamole or 1 $\mu$M Spiperone. Both saturation and competition binding data are analyzed by the non-linear least square curve-fitting program Ligand run on a digital Micro-PP-11 as described by Sunahara et al.

In an assay similar to the one described above, each of the title compounds of Example 1, 4 and 6–9 exhibited an $1C_{50}$ for the D4 receptor less than or equal to 0.11 $\mu$M and an $1C_{50}$ for the D2 receptor greater than 1.0 $\mu$M and less than 3.3 $\mu$m.

The present invention is illustrated by the following examples. It will be understood, however, that the invention is not limited to the specific details of these examples.

EXAMPLE 1

1-{3-[4-(5-Chloro-pyridin-2-yl)-piperazin-1-yl]-propyl}-1,3-dihydro-benzoimidazol-2-one A mixture of 1.14 gm of 2-piperazino 5-chloro pyridine, 1.35 gm of 1-(3-chloro propyl)-2,3-dihydro-1H-benzimidazol-2-one (available from Janssen) and 1.49 gm of diisopropylethylamine in 3 ml DMF and 30 ml toluene is kept for 12 hours at 110° C. Upon cooling to ambient temperature, 30 ml water is added and the mixture is extracted with chloroform ($CHCl_3$) and the extract is collected, washed with 20 ml water and dried over sodium sulfate ($Na_2SO_4$). The crude product (2.5 gm) which is obtained after removing the solvents is purified using chromatography: solid phase ($SiO_2$; 40 $\mu$m; Baker); eluant 2% methanol ($CH_3OH$) in methylene chloride ($CH_2Cl_2$). A sample of this purified material (1.2 gm) was transferred into its hydrochloride (mp: 200° C.) by treating an ethanolic suspension of this material with a mixture of ethyl ether/HCl.

EXAMPLE 2

4-[3-(2-Oxo-2,3-dihydro-benzoimidazol-1-yl)-propyl]-piperazine-1-carboxylic acid tert-butyl-ester A mixture of 5.0 gm of 1-t-butoxycarbonyl piperazine, 6.26 gm of 1-(3-chloro propyl)-2,3-dihydro-1H-benzimidazol-2-one (available from Janssen) and 4.16 gm diisopropylethylamine in 150 ml ethanol is kept for 12 hours at 80° C. Upon cooling to ambient temperature, 100 ml water is added and the mixture is extracted with chloroform ($CHCl_3$) and the extract is collected, washed with 20 ml water and dried over $Na_2SO_4$. After removing the solvents, 10 gm of a yellowish oil is obtained which is used without further purification.

EXAMPLE 3

1-[4-(3-piperazine-1-yl)propyl]-2,3-dihydro-1h-benzimidazol-2-one

A saturated solution hydrochloric acid in 2 ml methanol and of 0.43 gm of 1-[4-(3-)t-butoxycarbonyl)piperazine-1-yl)propyl]-2,3-dihydro-1H-benzimidazol-2-one is kept for 1 hour at 50° C. Upon cooling to ambient temperature, the solvent is removed, and the residue is suspended in 10 ml water made basic with aqueous ammonium hydroxide solution. The aqueous layer is extracted with $CHCl_3$. The $CHCl_3$ extract is collected, washed with 20 ml water and dried over Na₂SO₄. After removing the solvents, 0.207 gm of a yellowish oil is obtained which is used without further purification.

EXAMPLE 4

1-{3-[4-(5-Trifluoromethyl-pyridin-2-yl)-piperazine-1-yl]-propyl}-1,3-dihydro-benzoimidazol-2-one A mixture of 0.054 gm of 2-chloro 5-trifluoromethyl pyridine, 0.115 gm of 1-[4-(3-piperazine-1-yl)propyl]2,3-dihydro-1H-benzimidazol-2-one and 0.194 gm of diisopropylethylamine in 1.0 ml of 1-methyl-2-pyrrolidinone is kept for 3 hours at 150° C. Upon cooling to ambient temperature and addition of 10 ml water the mixture is acidified with concentrated hydrochloric acid and extracted 2×5 ml ethyl ether. The aqueous layer is then neutralized with aqueous ammonium hydroxide solution and extracted with ethyl acetate. The ethyl acetate extract is collected, washed with 20 ml water and dried over Na₂SO₄. The crude product (0.085 gm) obtained after removing the solvents is purified using chromatography: solid phase (SiO₂; 40 µm; Baker); eluent 2% CH₃OH in CHCl₃. A sample of this purified material (0.015 gm) was transferred into its hydrochloride (mp: 183° C.) by treating an ethanolic suspension of this material with a mixture of ethyl ether/HCl.

EXAMPLE 5

1-(5-Bromo pyrid-2-yl) piperazine

A mixture of 5.0 g of 1-t-butoxycarbonyl piperazine, 6.36 gm of 2,5-dibromopyridine and 10.4 gm diisopropylethylamine in 50 ml of 1-methyl-2-pyrolidinone is kept for 12 hours at 150° C. Upon cooling to ambient temperature and addition of 10 ml water, the mixture is acidified with concentrated hydrochloric acid heated for 15 minutes and upon cooling extracted 2×5 ml ethyl ether. The aqueous layer is then neutralized with aqueous ammonium hydroxide solution and extracted with ethyl acetate. The ethyl acetate extract is collected, washed with 20 ml water and dried over Na₂SO₄. The crude product (4.3 gm) obtained after removing the solvents solidifies upon standing. This material is used without further purification.

The title compounds of Example 6–9 were prepared using a procedure similar to those of Examples 1 and 4.

EXAMPLE 6

1-{3-[4-(6-(6-Chloro-pyridazin-3-yl)-piperazin-1yl]-propyl}-1,3-dihydro-benzimadazol-2-one mp: 242°–245° C.

EXAMPLE 7

1-[3-(2,3,5,6-Tetrahydro-[1,2'bipyrazinyl-4-yl)-propyl]-1,3-dihydro-benzimidazol-2-one mp: 262°–264° C.

EXAMPLE 8

1-{3-[4-(5-Bromo-pyridin-2-yl)-piperazin-1-yl]-propyl}-1,3-dihydro-benzoimidazol-2-one mp: 201°–202° C.

EXAMPLE 9

1-[3-(4-Pyridin-2-yl-piperazin-1-yl)propyl]-1,3-dihydro-benzoimidazol-2-one mp: 186° C.

We claim:

1. A compound of the formula

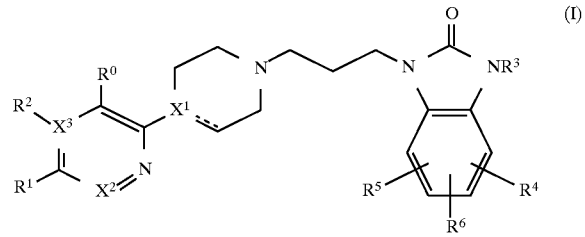

wherein $X^1$, $X^2$ and $X^3$ are independently selected from carbon and nitrogen;

$R^0$, $R^1$ and $R^2$ are independently selected from hydrogen, halo, $(C_1-C_6)$alkyl optionally substituted with from one to three fluorine atoms and $(C_1-C_6)$alkoxy optionally substituted with from one to three fluorine atoms;

$R^3$ is hydrogen, $(C_1-C_6)$alkyl or benzyl, wherein the phenyl moiety of said benzyl group may optionally be substituted with from one or more substituents, independently selected from halo, cyano, $(C_1-C_6)$alkyl optionally substituted with from one to three fluorine atoms, $(C_1-C_6)$alkoxy optionally substituted with from one to three fluorine atoms, $(C_1-C_6)$alkylsulfonyl, $(C_1-C_6)$alkylamino, amino, di-$(C_1-C_6)$alkylamino and $(C_1-C_6)$carboxamido;

$R^4$, $R^5$ and $R^6$ are independently selected from hydrogen, halo, cyano, $(C_1-C_6)$alkyl optionally substituted with from one to three fluorine atoms, $(C_1-C_6)$alkoxy optionally substituted with from one to three fluorine atoms, $(C_1-C_6)$alkylsulfonyl, $(C_1-C_6)$acylamino, (phenyl)[$(C_1-C_6)$acyl]amino, amino, $(C_1-C_6)$alkylamino and di-$(C_1-C_6)$alkylamino; and the dashed line represents an optional double bond;

with the proviso that when $X^3$ is nitrogen, $R^2$ is absent;

or a pharmaceutically acceptable salt thereof.

2. A compound according to claim 1 wherein $X^2$ is nitrogen.

3. A compound according to claim 2, wherein $R^1$ is bromine or chlorine.

4. A compound according to claim 1, wherein said compound is selected from the group consisting of:

1-[3-(4-pyridin-2-yl-piperazin-1-yl)-propyl]-1,3-dihydro-benzoimidazol-2-one;

1-{3-[4-(5-trifluoromethyl-pyridin-2-yl)-piperazin-1-yl]-propyl}-1,3-dihydro-benzoimidazol-2-one;

1-{3-[4-(5-chloro-pyridin-2-yl)-piperazin-1-yl]-propyl}-1,3-dihydro-benzoimidazol-2-one;

1-{3-[4(5-bromo-pyridin-2-yl)-piperazin-1-yl]-propyl}-1,3dihydro-benzoimidazol-2-one;

1-[3-(2,3,5,6-tetrahydro-[1,2]bipyrazinyl-4-yl)-propyl]-1,3-dihydro-benzoimidazol-2-one; and 1-{3-[4-(6-chloro-pyridazin-3-yl)-piperazin-1-yl]-propyl}-1,3-dihydro-benzoimidazol-2-one.

5. A pharmaceutical composition for treating a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, bacterial infections of the CNS, learning disorders, memory disorders, Parkinson's disease, depression, extrapyramidal side effects from neuroleptic agents, neuroleptic malignant syndrome, hypothalamic pituitary disorders, congestive heart failure, chemical dependencies, vascular and cardiovascular disorders, ocular disorders, dystonia, tardive dyskinesia, Gilles De LaTourette's syndrome and other hyperkinesias, dementia, ischemia, Parkinson's disease, akathesia and other movement disorders, hypertension and diseases caused by a hyperactive immune system such as allergies and inflammation in a mammal, comprising an amount of a compound according to claim 1 that is effective in treating such condition, and a pharmaceutical acceptable carrier.

6. A pharmaceutical composition for treating a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, meningitis and other bacterial infections of the CNS, learning disorders, memory disorders, Parkinson's disease, depression, extrapyramidal side effects from neuroleptic agents, neuroleptic malignant syndrome, hypothalamic pituitary disorders, congestive heart failure, chemical dependencies, vascular and cardiovascular disorders, ocular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising a dopaminergic effective amount of a compound according to claim 1 and a pharmaceutically acceptable carrier.

7. A pharmaceutical composition for treating a disease or condition, the treatment or prevention of which can be effected or facilitated by altering dopamine mediated neurotransmission in a mammal, comprising a dopaminergic effective amount of a compound according to claim 1 and a pharmaceutically acceptable carrier.

8. A pharmaceutical composition for treating a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, meningitis and other bacterial infections of the CNS, learning disorders, memory disorders, Parkinson's disease, depression, extrapyramidal side effects from neuroleptic agents, neuroleptic malignant syndrome, hypothalamic pituitary disorders, congestive heartfailure, chemical dependencies, vascular and cardiovascular disorders, ocular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising a D4 receptor binding effective amount of a compound according to claim 1 and a pharmaceutically acceptable carrier.

9. A pharmaceutical composition for treating a disease or condition, the treatment or prevention of which can be effected or facilitated by altering dopamine mediated neurotransmission in a mammal, comprising a D4 receptor binding effective amount of a compound according to claim 1 and a pharmaceutically acceptable carrier.

10. A method of treating a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, meningitis and other bacterial infections of the CNS, learning disorders, memory disorders, Parkinson's disease, depression, extrapyramidal side effects from neuroleptic agents, neuroleptic malignant syndrome, hypothalamic pituitary disorders, congestive heart failure, chemical dependencies, vascular and cardiovascular disorders, ocular disorders, dystonia, tardive dyskinesia, Gilles De La Tourefte's syndrome and other hyperkinesias, dementia, ischemia, Parkinson's disease, akathesia and other movement disorders, hypertension and diseases caused by a hyperactive immune system such as allergies and inflammation in a mammal, comprising administering to said mammal an amount of a compound according to claim 1 that is effective in treating such a condition.

11. A method of treating a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, meningitis and other bacterial infections of the CNS, learning disorders, memory disorders, Parkinson's disease, depression, extrapyramidal side effects from neuroleptic agents, neuroleptic malignant syndrome, hypothalamic pituitary disorders, congestive heart failure, chemical dependencies, vascular and cardiovascular disorders, ocular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising an administering to said mammal a dopaminergic effective amount of a compound according to claim 1.

12. A method of treating a disease or condition, the treatment of which can be effected or facilitated by altering dopamine mediated neurotransmission in a mammal, comprising administering to said mammal a dopaminergic effective amount of a compound according to claim 1.

13. A method of treating a condition selected from sleep disorders, sexual disorders, gastrointestinal disorders, psychosis, affective psychosis, nonorganic psychosis, personality disorders, psychiatric mood disorders, conduct and impulse disorders, schizophrenic and schizoaffective disorders, polydipsia, bipolar disorders, dysphoric mania, anxiety and related disorders, obesity, emesis, meningitis and other bacterial infections of the CNS, learning disorders, memory disorders, Parkinson's disease, depression, extrapyramidal side effects from neuroleptic agents, neuroleptic malignant syndrome, hypothalamic pituitary disorders, congestive heart failure, chemical dependencies, vascular and cardiovascular disorders, ocular disorders, dystonia, tardive dyskinesia, Gilles De La Tourette's syndrome and other hyperkinesias, dementia, ischemia, Parkinson's disease, akathesia and other movement disorders, hypertension and diseases caused by a hyperactive immune system such as allergies and inflammation in a mammal, comprising an administering to said mammal a D4 receptor binding effective amount of a compound according to claim 1.

14. A method of treating a disease or condition, the treatment or prevention of which can be effected or facilitated by altering dopamine mediated neurotransmission in a mammal, comprising administering to said mammal a D4 receptor binding effective amount of a compound according to claim 1.

15. A compound as claimed in claim 1 wherein the phenyl moiety of benzyl in the definition of $R^3$ may optionally be substituted with from one to three substituents.

* * * * *